United States Patent
Furlow, Jr.

(10) Patent No.: US 8,002,845 B2
(45) Date of Patent: *Aug. 23, 2011

(54) MATERIALS AND METHODS FOR SOFT TISSUE AUGMENTATION

(76) Inventor: Leonard T. Furlow, Jr., Gainesville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/618,737

(22) Filed: Nov. 15, 2009

(65) Prior Publication Data

US 2010/0063600 A1    Mar. 11, 2010

Related U.S. Application Data

(63) Continuation of application No. 10/812,724, filed on Mar. 29, 2004, now Pat. No. 7,655,048.

(60) Provisional application No. 60/459,937, filed on Apr. 2, 2003.

(51) Int. Cl.
*A61F 2/02*    (2006.01)

(52) U.S. Cl. .................................................... 623/23.73

(58) Field of Classification Search ..... 623/23.72–23.76
See application file for complete search history.

(56) References Cited

U.S. PATENT DOCUMENTS

| | | | |
|---|---|---|---|
| 5,336,263 A | 8/1994 | Ersek et al. | |
| 5,895,411 A | 4/1999 | Irie | |
| 6,280,191 B1 | 8/2001 | Gordon | |
| 6,284,284 B1 | 9/2001 | Naughton | |
| 6,328,745 B1 | 12/2001 | Ascherman | |
| 6,592,366 B2 | 7/2003 | Triaca et al. | |
| 6,695,781 B2 | 2/2004 | Rabiner et al. | |
| 6,866,663 B2 | 3/2005 | Edwards et al. | |
| 7,655,048 B2 * | 2/2010 | Furlow, Jr. ................. | 623/23.73 |

* cited by examiner

*Primary Examiner* — Bruce E Snow

(74) *Attorney, Agent, or Firm* — Saliwanchik, Lloyd & Eisenschenk

(57) ABSTRACT

The subject invention provides materials and methods for soft tissue augmentation. The materials and methods of the subject invention can, advantageously, be used to correct defects such as velopharyngeal insufficiency after cleft palate repair. Other uses include treatments for gastroesophageal acid-reflux, urinary incontinence, wrinkles and contour abnormalities.

4 Claims, No Drawings

MATERIALS AND METHODS FOR SOFT TISSUE AUGMENTATION

CROSS-REFERENCE TO A RELATED APPLICATION

This application is a continuation application of application Ser. No. 10/812,724, filed Mar. 29, 2004 now U.S. Pat. No. 7,655,048; which claims the benefit of U.S. provisional application Ser. No. 60/459,937, filed Apr. 2, 2003, which are incorporated herein by reference in their entirety.

BACKGROUND OF INVENTION

Orofacial clefts, including clefts of the palate, are among the most common human congenital abnormalities. Cleft palates are characterized by a partial or total lack of fusion of palatal shelves that may involve primarily the soft palate (velum) or the entire (hard and soft) palate. In the United States, an estimated twenty infants are born with an orofacial cleft on an average day.

The patient with an unrepaired cleft palate will have impaired speech. The muscles of the palate elevate the normal soft palate (velum) to seal against the posterior pharyngeal wall to block airflow and sound from the nasal cavity during English speech for all sounds except "m", "n" and "ng". A cleft renders the palatal valve (the velopharyngeal valve) incompetent, which gives the patient's speech a characteristic nasal quality which is difficult to impossible to understand. Unfortunately, surgically repairing the cleft provides a valve that can completely and normally close for speech in only some 20% to 90% of patients. When valving function is poor, a condition termed velopharyngeal insufficiency, one of several second operations may be performed to improve the function of the velopharyngeal valve. However, a very significant number of patients with repaired clefts, up to 45%, speak clearly enough to communicate, even though valve closure is not complete. Because of the risk, pain and cost of the secondary operations, these patients usually remain untreated even though their speech sounds abnormal enough to be socially curious. It is primarily for these patients that the invention herein described is designed, although it may also prove to be an effective treatment for patients now undergoing larger operations for velopharyngeal insufficiency.

When the repaired cleft palate has some mobility but is not long enough to seal completely against the posterior pharyngeal wall, one method of treatment has been to augment the posterior pharyngeal wall forward toward the soft palate so that the palate can reach and seal. To accomplish this, various materials have been placed in the tissues of the posterior pharyngeal wall to bulge it forward. The simplest method has been to place a fluid material such as silicone or a paste of Teflon® particles by injection. However, because of the potential for migration of the materials away from the site of injection (with loss of the mound) to lymph nodes, tissue planes or even lungs or brain, these methods have not gained approval for clinical use.

Various treatments for cleft palate repair have been proposed. See, for example, U.S. Pat. Nos. 6,695,781; 6,592,366; 6,328,745; 6,284,284; and 6,280,191. However, better treatments are still needed.

A tissue-inert material that could be injected that would remain at the injection site would be helpful to the many patients with repaired cleft palates whose velopharyngeal valves do not close properly for speech.

BRIEF SUMMARY

The subject invention provides materials and methods for soft tissue augmentation. The materials and methods of the subject invention can, advantageously, be used to augment soft tissue planes such as the posterior pharyngeal wall. Other uses include treatments to displace a vocal cord, for gastroesophageal acid-reflux, urinary incontinence, tissue and scar depressions, wrinkles, and to produce other contour changes and tissue augmentations.

In a preferred embodiment, the subject invention involves the injection of hollow-cylinder pellets such as, for example, doughnut-shaped pellets, to a site where soft tissue augmentation is desired. The pellets are made of an inert material that is physiologically non-reactive. In a particularly preferred embodiment, the pellets are slippery (non-stick) and approximately the density of soft tissue. Specifically exemplified herein are cylindrical or doughnut-shaped particles made from Teflon®, or other appropriate material as described herein.

A further aspect of the subject invention are methods for soft tissue augmentation. These methods preferably involve the injection of hollow-cylinder pellets at a site where soft tissue augmentation is needed. Advantageously, the presence of the hollow conduit running through the pellets used according to the subject invention provides a site for the pellets to be effectively anchored in place by the growth of surrounding cells and tissues through the central lumen of each particle.

Yet another aspect of the subject invention pertains to devices to efficiently, effectively, and accurately deliver the pellets of the subject invention to a site where soft tissue augmentation is desired. In a preferred embodiment, the device is a syringe that is specifically adapted to deliver the pellets of the subject invention to a desired location.

In a further embodiment, the subject invention provides medical compositions comprising hollow-cylinder pellets for use in augmenting soft tissue. The compositions comprise medical-grade pellets, optionally in an appropriate pharmaceutical carrier. The composition may, optionally, further comprise additional appropriate ingredients including, but not limited to, growth factors, analgesics, and antibiotics. In one embodiment these additional ingredients may be contained in the lumen of the pellets.

DETAILED DISCLOSURE

The subject invention provides unique and advantageous materials and methods for soft tissue repair and augmentation. The materials and methods of the subject invention can, advantageously, be used to augment the posterior pharyngeal wall for correction of velopharyngeal insufficiency after cleft palate repair. Other uses would be apparent to those skilled in the art and include treatments for gastroesophageal acid-reflux, urinary incontinence, contour abnormalities and changes, and wrinkles.

In a preferred embodiment, the subject invention involves the injection of hollow-cylinder pellets such as, for example, doughnut-shaped pellets, to a site where soft tissue augmentation is desired. The pellets may be any shape, so long as they have a hollow space running therethrough. In additional embodiments, the pellets could also be, for example, spherical (or any other shape) with a hollow tunnel passing therethrough.

The pellets are, preferably, made of an inert material that is physiologically non-reactive. In a particularly preferred embodiment the pellets are non-biodegradable, slippery (non-stick) and lightweight (approximately the density of soft tissue to avoid being acted upon by gravity). The pellets may be made from, for example, polypropylene, nylon, dacron, silicone, and polyurethane. Specifically exemplified herein are truncated hollow-cylinder particles made from polytetrafluoroethylene (such as Teflon®). The pellets could also be made of a material, such as a bioactive glass (BioGlass®) that promotes tissue growth.

A further aspect of the subject invention includes methods used for soft tissue augmentation. These methods preferably involve the injection of hollow-cylinder pellets, as described herein, at a site where soft tissue augmentation is desired. Advantageously, after injection of the pellets, the fibrous tissue that forms around each injected pellet, will also grow through the hollow central conduit of the pellet, effectively anchoring the pellet in place, preventing migration of the pellets.

Yet another aspect of the subject invention pertains to devices to efficiently, effectively, and accurately deliver the pellets of the subject invention to a site where soft tissue augmentation is desired. In a preferred embodiment, the device is a syringe that is specifically adapted to deliver the pellets of the subject invention to a desired location.

In a further embodiment, the subject invention provides medical compositions comprising hollow-cylinder pellets for use in augmenting soft tissue. The compositions comprise medical-grade pellets, optionally in an appropriate pharmaceutical carrier. The composition may, optionally, further comprise additional appropriate ingredients including, but not limited to, growth factors, analgesics, and antibiotics.

In a specific embodiment, the subject invention provides useful and novel, medical-grade, non-absorbable minimally-reactive materials and their use, for posterior pharyngeal wall implantation for creating a ridge, mound or lump to permit the velopharyngeal valve to close. Thus, as a result of this unique and advantageous procedure, the soft palate (velum) is able to close against the posterior pharyngeal wall.

An important aspect of the subject invention is the shape of particles of the injectable material. Preferably, the particles have the shape of a doughnut or a short cylinder.

The particles preferably have the following characteristics:
1) Inner diameter that will permit tissue ingrowth;
2) Wall thickness that will keep cylinders from locking together,
3) Outer diameter and length that will permit injection through a #14 to #16 gauge needle; and
4) An overall uniform size such that the particles are too large for cells (phagocytes) to cause to migrate away from the area of injection.

The cylinder may have, for example, an outer diameter of from about 100 µm to about 500 µm. Preferably, the outer diameter is from about 200 µm to about 400 µm. The inner diameter is preferably from about 50 µm to about 300 µm. More preferably, the inner diameter is from about 100 µm to about 200 µm. The inner diameter is selected to be large enough to allow the ingrowth of capillaries and fibrous tissue through the lumen or hollow conduit from both ends. Accordingly, in a specific embodiment, the cylinder has an outer diameter of about 300 µm and an inner diameter of about 150 µm. Thus, the thickness of the wall of the cylinder, in this embodiment is about 75 µm.

The length of the cylinder may be from about ½ to 2 times its outer diameter. In a preferred embodiment, the length may be from about 75 µm to about 750 µm. Even more preferably, the cylinder is about 300 µm to 500 µm in length.

In a preferred embodiment, the inner diameter is large enough to allow ingrowth of tissue. The thickness of the wall of the tube is sufficient to prevent the hollow cylinder from collapsing, thereby occluding the hollow center. The outer diameter and length of the particles should be sufficient to allow ingrowth while still being small enough so that a composition made up of these particles passes readily through a 12-20 gauge needle, and preferably through a 14-18 gauge needle.

This shape and size permits growth of fibrous tissue through the central hole, which anchors the particle in place and prevents its migration.

In a preferred embodiment, the density of the composition comprising the particles as described herein is designed to match the density of the tissue where the composition will be placed. This helps to avoid a differential effect by gravity. Thus, the composition will not be inclined to settle or otherwise separate from the surrounding tissue. Generally, the density will be close to 1 gram/cm$^3$. In a preferred embodiment the density will be within 5% of the surrounding tissue, more preferably within 1%. Thus, for example, the composition would typically have a density of 0.95 to 1.05 or, more preferably from 0.99 to 1.01.

In view of its use in treating humans and animals in need of soft tissue augmentation, the composition of the subject invention is preferably sterile.

In one embodiment, the subject invention provides a sterile composition comprising particles as described herein wherein this composition can be loaded into an appropriate delivery device, such as a syringe or endoscopic device. In one embodiment, this loading process can take place at or near the time of treating a patient. Thus the loading is done by the physician or other person involved in the procedure. In another embodiment, the delivery device is manufactured with the augmentation composition already loaded such that the device is ready for immediate use. In this embodiment, preferably, the entire assembly is manufactured and delivered under sterile conditions.

In one embodiment, the particles are not suspended in any other material. In other embodiments an appropriate fluid can be used as a medium to facilitate delivery of the particles. The fluid may comprise, for example, glycerine.

The particles and/or composition comprising the particles should behave as a fluid to facilitate delivery to the desired location. Thus, the particles are preferably smooth and are not able to nest to any significant extent. The particles are also sufficiently sturdy so that they are not smashed during storage or the delivery process.

Despite the fluid-like nature of the augmentation composition of the subject invention, the composition does not extensively migrate from its point of deposition in the patient's soft tissue. The lack of migration is due to the unique nature of the particles, which match the tissue in terms of density and which are designed to permit efficient tissue ingrowth that holds the particles in place.

In a preferred embodiment, the subject invention also provides methods for the treatment of velopharyngeal insufficiency after cleft palate repair or from other causes.

The materials and methods of the subject invention can also be used to efface skin wrinkles, narrow the urethral and/or the gastro esophageal passage, displace a vocal cord or cords, and to produce a soft tissue bulge or fill elsewhere in the body of an individual in need of such treatment.

In a specific embodiment, for subcutaneous injection, the material will be of a color that is not visible through the skin, such as tan, translucent or clear. Pink or red material could be used for augmentation of the lips or other areas in or around the mouth.

The term "individual(s)" is defined as a single mammal to which is administered a compound or composition of the present invention. The mammal may be, for example a mouse, rat, pig, horse, rabbit, goat, pig, cow, cat, dog, or human. In a preferred embodiment, the individual is a human.

Following are examples that illustrate procedures for practicing the invention. These examples should not be construed as limiting. All percentages are by weight and all solvent mixture proportions are by volume unless otherwise noted.

Example 1

Particle Size

1. Inside diameter (I.D.): The central hole or tunnel of the cylindrical or doughnut-shaped device, which must be large enough to permit fibrous tissue ingrowth: minimum I.D.=15/1000 mm=15 μm.

Maximum inside diameter of the device:

Defined by maximum O.D.×maximum I.D./O.D. ratio.

2. Outside diameter (O.D.): The cylindrical or doughnut-shaped device must be of a size that will permit the device to be injected through a large-bore needle (i.e. a #14 gauge needle).

Minimum O.D. of the device:

Defined by minimum I.D./maximum I.D./O.D. ratio

3. I.D./O.D. ratio: Maximum ratio defined by I.D. and O.D. sizes that will not permit "nesting" of one device into another, which would interfere with flow during injection, and tissue deposition as individual particles, and by the stiffness of the device material, which must substantially withstand deformation:

Maximum I.D./O.D. ratio=0.9

Minimum I.D./O.D. ratio defined by minimum I.D./Maximum O.D.=0.0015/1.0=0.0015.

I.D./O.D. ratio may therefore range from 0.0015 to 0.9

Maximum I.D.=maximum O.D.×maximum I.D./O.D. ratio=1.0 mm×0.9=0.9 mm.

Minimum O.D.=minimum I.D./maximum I.D./O.D. ratio=0.0015 mm/0.9=0.00167 mm.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

I claim:

1. A method for soft tissue repair or augmentation wherein said method comprises the placement of hollow-cylinder pellets at a site where repair or augmentation is desired, wherein said pellets have a hollow conduit running therethrough, such that when the pellets are placed at the location where repair or augmentation is desired, fibrous tissue and its capillaries grow into the hollow conduits thereby preventing migration of the pellets, wherein the pellets are made from an inert physiologically non-reactive material; and wherein the pellets are smooth, have an outer diameter of 100 μm to 500 μm, an inner diameter of 50 μm to 300 μm, a length of 300 μm to 500 μm, a maximum ratio of inner diameter to outer diameter of 0.9 and are sufficiently uniform in dimension so that the pellets cannot nest one inside another.

2. The method, according to claim 1, wherein said pellets are made from a material selected from the group consisting of polyethylene, polypropylene, nylon, dacron, silicone, and polyurethane.

3. The method, according to claim 2, wherein said particles are made from polytetrafluoroethylene.

4. The method, according to claim 1, for use in effacing wrinkles.

* * * * *